United States Patent
Yang

(10) Patent No.: US 11,471,474 B2
(45) Date of Patent: Oct. 18, 2022

(54) PHARMACEUTICAL OR COSMETIC COMPOSITION FOR PREVENTING OR TREATING HAIR LOSS OR PROMOTING HAIR GROWTH

(71) Applicant: Mi Gyoung Yang, Seoul (KR)

(72) Inventor: Mi Gyoung Yang, Seoul (KR)

(*) Notice: Subject to any disclaimer, the term of this patent is extended or adjusted under 35 U.S.C. 154(b) by 0 days.

(21) Appl. No.: 17/042,580

(22) PCT Filed: Mar. 28, 2019

(86) PCT No.: PCT/KR2019/003638
§ 371 (c)(1),
(2) Date: Sep. 28, 2020

(87) PCT Pub. No.: WO2019/194470
PCT Pub. Date: Oct. 10, 2019

(65) Prior Publication Data
US 2021/0015840 A1      Jan. 21, 2021

(30) Foreign Application Priority Data

Apr. 2, 2018   (KR) .................. 10-2018-0038127

(51) Int. Cl.
| | |
|---|---|
| *A61K 38/18* | (2006.01) |
| *A61K 8/60* | (2006.01) |
| *A61K 8/64* | (2006.01) |
| *A61K 8/67* | (2006.01) |
| *A61P 17/14* | (2006.01) |
| *A61Q 7/00* | (2006.01) |
| *A61K 31/7076* | (2006.01) |
| *A61K 31/4188* | (2006.01) |
| *A61K 38/17* | (2006.01) |

(52) U.S. Cl.
CPC ............ *A61K 31/7076* (2013.01); *A61K 8/60* (2013.01); *A61K 8/64* (2013.01); *A61K 8/673* (2013.01); *A61K 31/4188* (2013.01); *A61K 38/1703* (2013.01); *A61K 38/18* (2013.01); *A61K 38/1808* (2013.01); *A61K 38/1825* (2013.01); *A61K 38/1858* (2013.01); *A61K 38/1866* (2013.01); *A61P 17/14* (2018.01); *A61Q 7/00* (2013.01)

(58) Field of Classification Search
CPC ............ A61K 31/4188; A61K 31/7076; A61K 38/1703; A61K 38/18; A61K 38/1808; A61K 38/1825; A61K 38/1858; A61K 38/1866; A61K 8/60; A61K 8/64; A61K 8/673; A61K 8/67; A61P 17/14; A61Q 7/00
See application file for complete search history.

(56) References Cited

U.S. PATENT DOCUMENTS

| | | | |
|---|---|---|---|
| 2010/0203055 A1 | 8/2010 | Imamura et al. | |
| 2012/0189607 A1* | 7/2012 | Kim ................. | A61P 15/08 514/47 |
| 2013/0224177 A1* | 8/2013 | Kim ................. | A61K 31/708 514/47 |
| 2021/0069228 A1 | 3/2021 | Yang | |

FOREIGN PATENT DOCUMENTS

| | | |
|---|---|---|
| KR | 10-2003-0062005 | 7/2003 |
| KR | 10-2003-0062605 A | 7/2003 |
| KR | 10-2006-0059557 | 6/2006 |
| KR | 10-2012-0014788 A | 2/2012 |
| KR | 10-2015-0117609 A | 10/2015 |
| KR | 10-2016-0060914 A | 5/2016 |
| KR | 10-2016-0119690 | 10/2016 |
| KR | 10-2017-0008501 | 1/2017 |
| KR | 10-1951283 B1 | 2/2019 |
| WO | 2019093608 A | 5/2019 |

OTHER PUBLICATIONS

Shuto et al., "Total Synthesis of Cyclic ADP-carbocyclic-ribose, a Stable Mimic of Ca2+-Mobilizing Second Messenger Cyclic ADP-Ribose," J. Am. Chem. Soc., 2001, 123: 8750-8759. (Year: 2001).*
Alopecia from Merck Manual, pp. 1-9. Accessed Nov. 2, 2020. (Year: 2020).*
Alopecia Areata from Merck Manual, pp. 1-3. Accessed Nov. 2, 2020. (Year: 2020).*
Takahashi, J., et al., "Deficit of CD38/cyclic ADP-ribose is differentially compensated in hearts by gender", Biochemical and Biophysical Research Communications 312 (2003) 434-440.
International Search Report for International Application No. PCT/KR2019/003638, "Pharmaceutical or Cosmetic Composition for Preventing or Treating Hair Loss or Promoting Hair Growth", dated Jul. 4, 2019.
Written Opinion for International Application No. PCT/KR2019/003638, "Pharmaceutical or Cosmetic Composition for Preventing or Treating Hair Loss or Promoting Hair Growth", dated Jul. 4, 2019.
Dippel, E., et al., "Distribution of Constitutive Nitric Oxide Synthase Immunoreactivity and NADPH-Diaphorase Activity in Murine Telogen and Anagen Skin", Nitric Oxide Synthase, 103(1): 112-115, Jul. 1994.

(Continued)

*Primary Examiner* — Julie Ha
(74) *Attorney, Agent, or Firm* — Hamilton, Brook, Smith & Reynolds, P.C.

(57) ABSTRACT

A pharmaceutical composition or a cosmetic composition treating hair loss, or promoting hair growth is described. The composition comprises cyclic adenosine diphosphate ribose (cADPR) or derivatives thereof or comprises at least one selected from one or more naturally occurring amino acid or salt thereof, one or more growth factor, noggin, one or more saturated or unsaturated C8 to C18 long chain fatty acid or salt thereof, one or more active factor and one or more water-soluble vitamin or salt thereof in addition to cyclic ADP ribose. The composition exhibits an excellent effect of treating hair loss and promoting hair growth and can be safely used regardless of sex or age.

9 Claims, 3 Drawing Sheets

(56) References Cited

OTHER PUBLICATIONS

International Search Report for International Application No. PCT/KR2018/006140, "Pharmaceutical or Cosmetic Composition for Preventing or Treating Hair Loss or Promoting Hair Growth", dated Sep. 5, 2018.
Written Opinion for International Search Report for International Application No. PCT/KR2018/006140, "Pharmaceutical or Cosmetic Composition for Preventing or Treating Hair Loss or Promoting Hair Growth", dated Sep. 5, 2018.
Chini EN. et al., "CD38 is the major enzyme responsible for synthesis of nicotinic acid-adenine dinucleotide phosphate in mammalian tissues", Biochem J 362:125-130, 2002.
Berridge G. et al., "Metabolism of the novel Ca2+-mobilizing messenger nicotinic acid-adenine dinucleotide phosphate via a 2«-specific Ca2+-dependent phosphatase", Biochem. J., 365: 295-301, 2002.
Aarhus R. et al., "ADP-ribosyl Cyclase and CD38 Catalyze the Synthesis of a Calcium-mobilizing Metabolite from NADP" J Biol Chem., 270(51): 30327-30333, 1995.
Graeff, R., et al., Acidic Residues at the Active Sites of CD38 and ADP-ribosyl Cyclase Determine Nicotinic Acid Adenine Dinucleotide Phosphate (NAADP) Synthesis and Hydrolysis Activities:, The Journal of Biological Chemistry. 281 (39): 28951-7, Sep. 29, 2006.
International Preliminary Report on Patentability for International Application No. PCT/KR2018/006140, "Pharmaceutical or Cosmetic Composition for Preventing or Treating Hair Loss or Promoting Hair Growth", dated May 19, 2020.
International Preliminary Report on Patentability for International Application No. PCT/KR2019/003638, "Pharmaceutical or Cosmetic Composition for Preventing or Treating Hair Loss or Promoting Hair Growth", dated Oct. 6, 2020.
Non-Final Office Action for U.S. Appl. No. 16/763,392 "Pharmaceutical or Cosmetic Composition for Preventing or Treating Hair Loss or Promoting Hair Growth" dated Apr. 25, 2022.

\* cited by examiner

[Fig. 1]
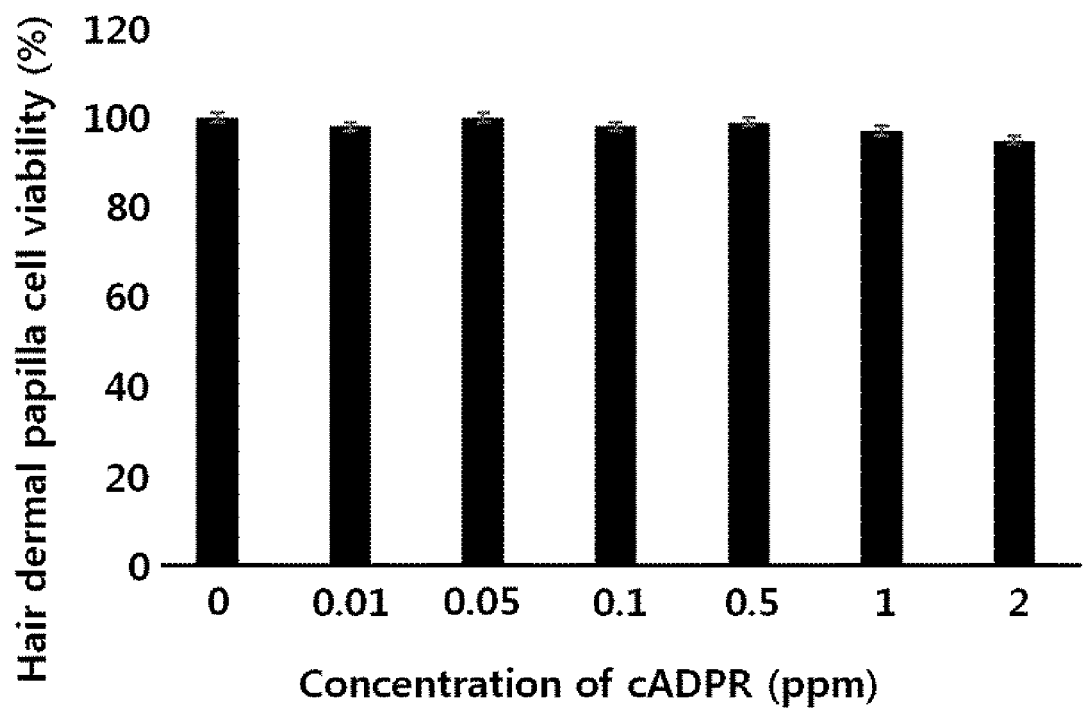
[Fig. 2]
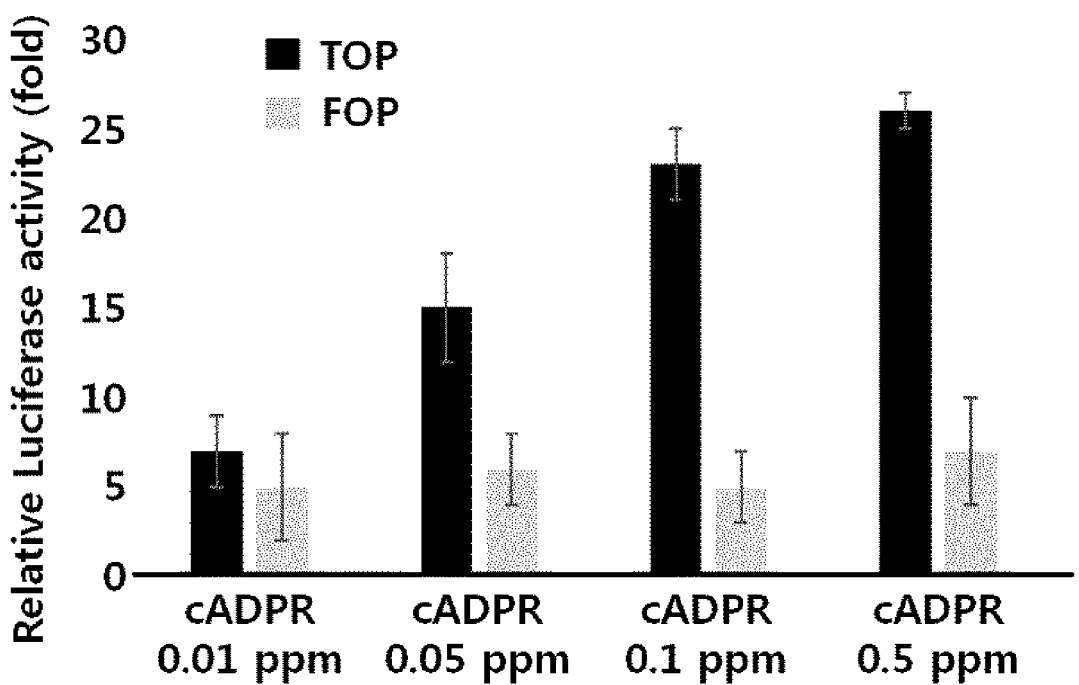

[Fig. 3]
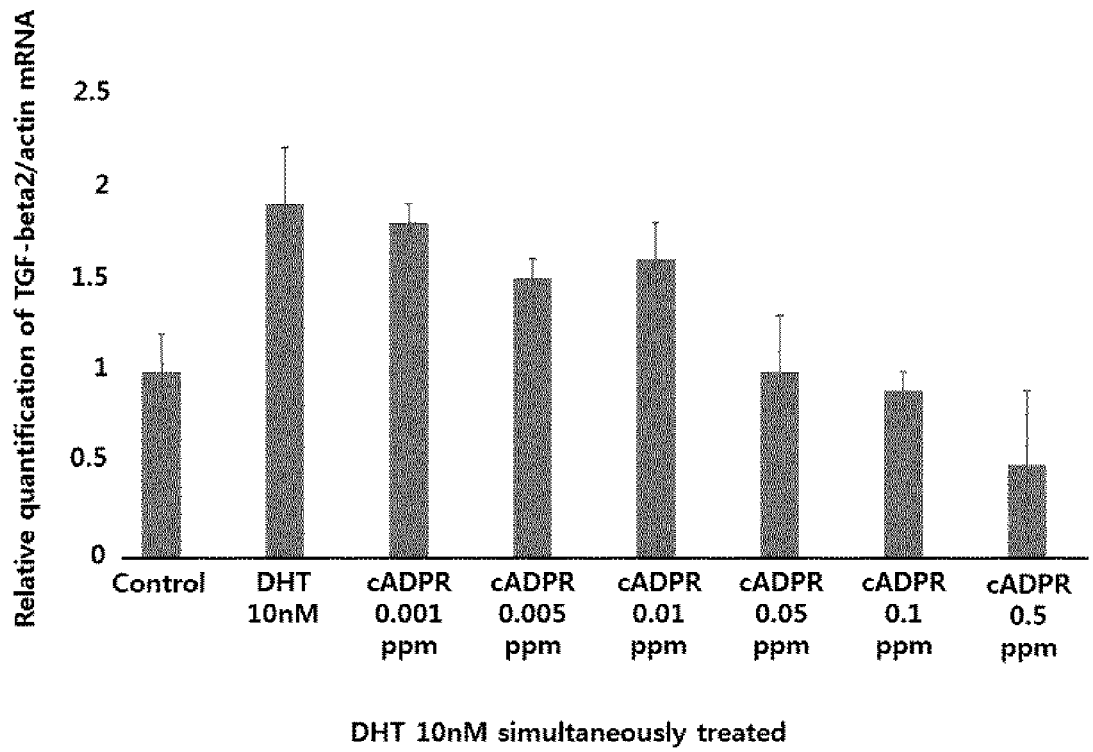
[Fig. 4]
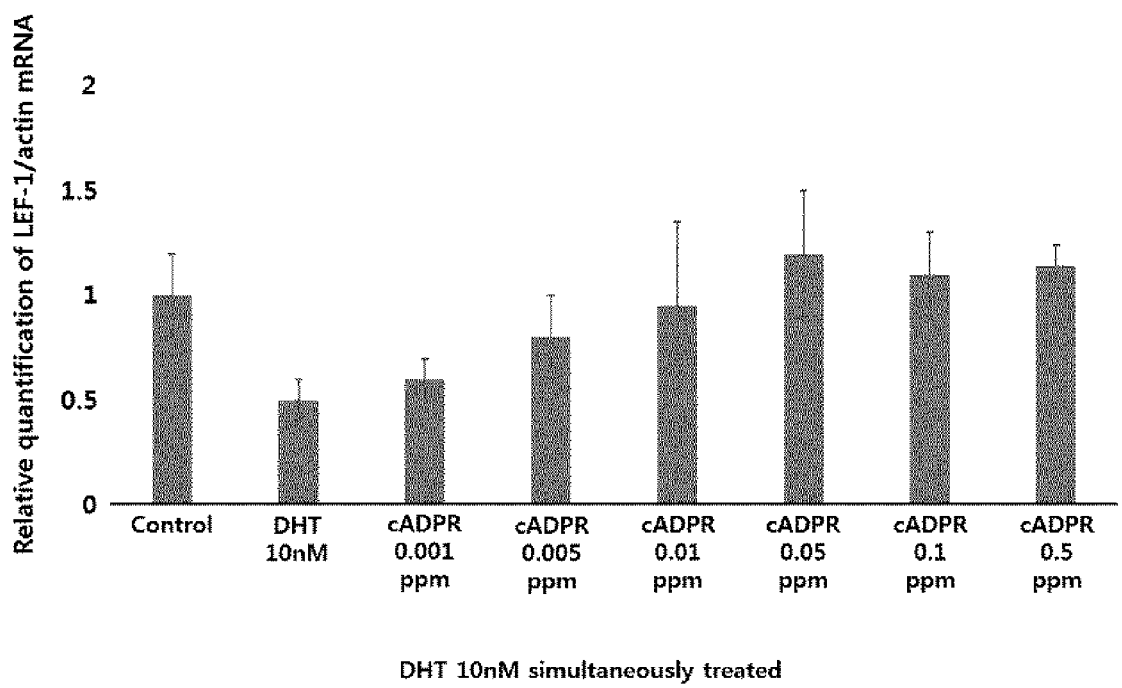

[Fig. 5]
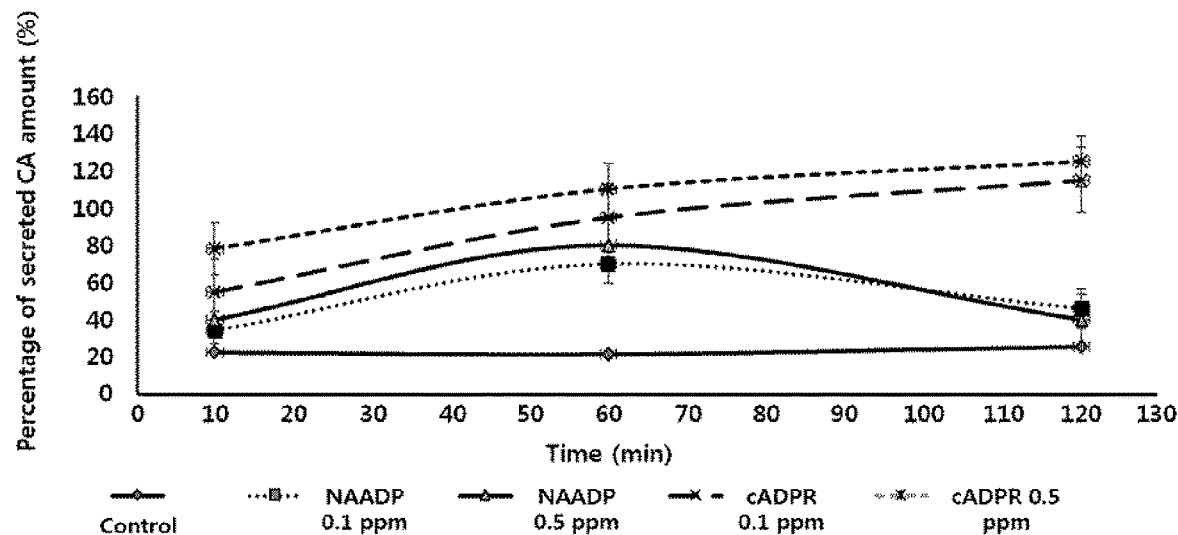
[Fig. 6]
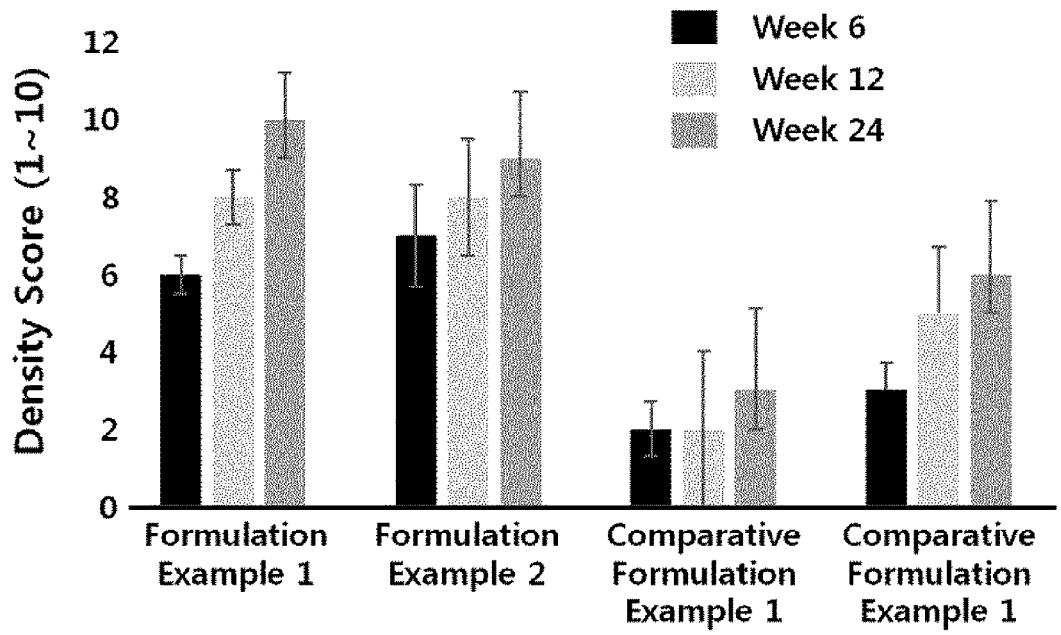

PHARMACEUTICAL OR COSMETIC COMPOSITION FOR PREVENTING OR TREATING HAIR LOSS OR PROMOTING HAIR GROWTH

This application is the U.S. National Stage of International Application No. PCT/KR2019/003638, filed Mar. 28, 2019, which designates the U.S., published in English, and claims priority under 35 U.S.C. § 119 or 365(c) to KR Application No. 10-2018-0038127, filed Apr. 2, 2018. The entire teachings of the above applications are incorporated herein by reference.

TECHNICAL FIELD

The present invention relates to a pharmaceutical composition or a cosmetic composition for preventing or treating hair loss, or promoting hair growth. More particularly, the present invention relates to a pharmaceutical composition or a cosmetic composition for preventing or treating hair loss, or promoting hair growth, comprising cyclic ADP Ribose (cADPR) or salt thereof, and at least one selected from the group comprising one or more nature-derived amino acid or salt thereof, one or more growth factor, noggin, one or more saturated or unsaturated C8 to C18 long chain fatty acid or salt thereof, one or more active factor and one or more water-soluble vitamin or salt thereof.

BACKGROUND ART

It has been known that hair loss is caused by local infections, endocrine disorders, genetic factors and autoimmunity as well as already known genetic causes. Recently, hair loss has been shown not only in middle-aged and elderly men but also in women or younger people. Thus, as the need for prevention and treatment of such hair loss has increased, research is being carried out on substances having various efficacy in overcoming hair loss.

Drugs currently used to prevent or treat hair loss and promote hair growth include vasodilators to circulate enough blood in the scalp, female hormone drugs to inhibit an action of male hormone, inhibitors inhibiting an activity of 5α-reductase that converts testosterone into 5-dihydrotestosterone (5-DHT), and the like.

In particular, examples of the vasodilators include capronium chloride, minoxidil and the like, examples of the female hormone drugs include estrogen, estradiol, progesterone and the like, and examples of the 5α-reductase activity inhibitors include finasteride, dutasteride, pentadecanoic acid, and the like. Among them, minoxidil has been prescribed for patients with severe hypertension as oral vasodilators and pharmacologically known as directly relaxing a smooth muscle of peripheral artery and is used as therapy for androgenetic alopecia.

However, the currently used preparations for preventing and treating hair loss and promoting hair growth are insufficient in their effects or have various problems such as side effects.

For example, since 5α-reductase inhibitors act on prostate as well as scalp, it may cause a decline in male sexual function, such as a decline in sexual desire or impotence, or a decline in ejaculation. Particularly, the side effects may occur for fertile woman that can interfere with the genital formation of a male fetus.

Recently, in order to overcome these side effects, research is being actively conducted on the compositions for preventing and treating hair loss and promoting hair growth by promoting the differentiation and proliferation of human hair dermal papilla cells.

In particular, human hair dermal papilla cells lead to the formation of hair at an early stage of an anagen phase of hair and then secrete substances that continue hair growth. Further, hair follicles degenerate as the cell stops the secretion of signal substances when it enters a categen phase. At this time, the normal hair enters anagen phase again as new hair follicles are formed through the differentiating of the stem cells of hair by hair dermal pailla cells in a telogen phase. However, if the telogen phase lasts or hair enters a categen phase in early stages due to various causes and thus does not have a sufficient period of anagen phase, hair loss may proceed or hair growth may be suppressed.

Particularly, calcium in the endoplasmic reticulum of hair dermal papilla cells acts as a signal transduction pathway to promote the differentiation of the papillary stem cells. At this time, when signal transduction pathway of Wnt/β-catenin is activated, the papillary stem cells differentiate into hair cells, enter an anagen phase and maintain a normal growth cycle. Further, when Wnt/β-catenin signal transduction pathway is activated, various growth factors such as epidermal growth factor (EGF), fibroblast growth factor (FGF) and the like are secreted in hair dermal papilla cells, which help to maintain a normal growth cycle. On the other hand, it is known that when signal transduction substances such as Dickkopf-related protein 1 (DKK1), transforming growth factor (TGF) or bone morphogenetic protein (BMP) and the like that cause catagen phase are inhibited due to the action of hair loss inducing hormone such as DHT in the cell, an anagen phase is normally maintained, and entry into a catagen phase is suppressed. As a result, an anagen phase shortened by various causes is prolonged, hair growth is promoted, hair loss is suppressed, and hair growth effect is expressed.

In this regard, Korean Patent Publication No. 2015-0117609 describes that NAADP which is synthesized by an ADP-ribosyl cyclase comprising CD38 is used in regulating the intracellular concentration of calcium. However, NAADP is known to act only as an early signal for intracellular calcium secretion and NADP can be converted into NAADP only under acidic pH. Further, it is difficult to stably maintain the calcium concentration due to limited calcium content in an acidic vesicle. Therefore, it has a limitation in achieving hair growth effect because of sustained differentiation of hair dermal papilla cells into hair cells.

Thus, it is necessary to develop a safe preparation that has a sustained and excellent effect in preventing or treating hair loss or promoting hair growth under various pH conditions and is applicable irrespective of age and sex.

DISCLOSURE OF INVENTION

Technical Problem

The purpose of the present invention is to provide a pharmaceutical composition or a cosmetic composition with an excellent effect in prevention or treatment of hair loss or promotion of hair growth that can prevent, improve or treat hair loss and promote hair growth through promotion of human hair dermal papilla cell proliferation.

Solution to Problem

In order to achieve the purpose, the present invention provides a pharmaceutical composition comprising a compound having a structure represented by the following Formula (I) or salt thereof:

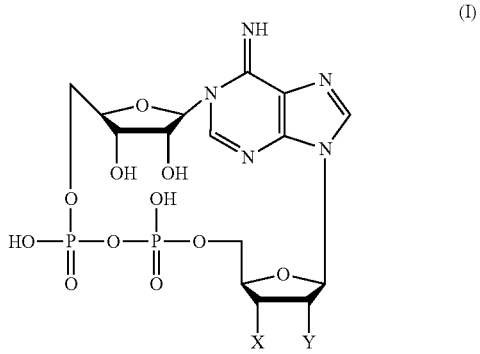

wherein,

X and Y are each independently selected from the group consisting of OH, CHO, COOH, SH and NH$_2$.

The present invention also provides a pharmaceutical composition and a cosmetic composition comprising at least one selected from the group comprising one or more nature-derived amino acid or salt thereof, one or more growth factor, noggin, one or more saturated or unsaturated C8 to C18 long chain fatty acid or salt thereof, one or more active factor and one or more water-soluble vitamin or salt thereof, in addition to a compound having the structure represented by the above Formula (I) or salt thereof.

Advantageous Effects of Invention

The pharmaceutical composition or cosmetic composition according to the present invention can be safely used regardless of sex and age by comprising a compound having the structure represented by Formula (I) or salt thereof. Further, since the composition can stably maintain the calcium concentration of endoplasmic reticulum in a human hair dermal papilla cell and activate Wnt/β-catenin signal transduction pathway even when the papilla cell condition is of neutral or basic pH, it exhibits an excellent effect of preventing or treating hair loss and promoting hair growth by promoting differentiation of papillary stem cells and such effect can last for a long time.

BRIEF DESCRIPTION OF DRAWINGS

FIG. 1 is a graph showing the results of cytotoxicity test in the human hair dermal papilla cells according to Experimental Example 1.

FIG. 2 is a graph showing the results of measuring the effect of activating β-catenin signal transduction in the human hair dermal papilla cells according to Experimental Example 2.

FIG. 3 is a graph showing the results of measuring the expression level of TGF-β2 gene in the human hair dermal papilla cells according to Experimental Example 3.

FIG. 4 is a graph showing the results of measuring the expression level of LEF-1 gene in the human hair dermal papilla cells according to Experimental Example 3.

FIG. 5 is a graph showing the results of measuring the duration time of calcium concentration in the human hair dermal papilla cells according to Experimental Example 5.

FIG. 6 is a graph showing the test results for the hair density in a human body according to Experimental Example 6.

BEST MODE FOR CARRYING OUT THE INVENTION

The present invention is described in detail below.

The present invention is related to a pharmaceutical composition for preventing or treating hair loss, or promoting hair growth comprising a compound having a structure represented by the following Formula (I) or salt thereof:

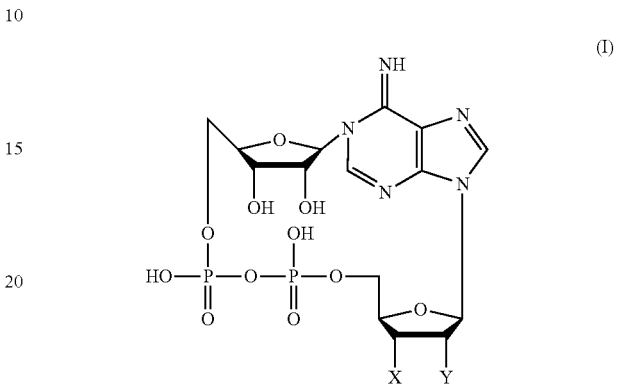

wherein,

X and Y are each independently selected from the group consisting of OH, CHO, COOH, SH and NH$_2$.

The present invention is also related to a pharmaceutical composition for preventing or treating hair loss, or promoting hair growth and a cosmetic composition for preventing or improving hair loss, or promoting hair growth, comprising a compound having the structure represented by the above Formula (I) or salt thereof; and at least one selected from the group comprising one or more nature-derived amino acid or salt thereof, one or more growth factor, noggin, one or more saturated or unsaturated C8 to C18 long chain fatty acid or salt thereof, one or more active factor and one or more water-soluble vitamin or salt thereof.

In one embodiment of the invention, the compound having the structure represented by the above Formula (I) may be cyclic ADP ribose (cADPR).

Generally, when the intracellular pH of human hair dermal papilla cells is acidic, NADP is converted into NAADP by CD38 gene. However, when the pH is not acidic, i.e., is neutral or basic, NADP is synthesized into cADPR by CD38 gene.

The present inventors have completed the present invention after confirming their finding that the compound of Formula (I) comprising such cADPR or salt thereof promotes differentiation and proliferation of hair follicle stem cells and human hair dermal papilla cells by stably maintaining calcium concentration in the endoplasmic reticulum of a human hair dermal papilla cell and activating Wnt/β-catenin signal transduction pathway, thereby exhibiting effect of prevention or treatment of hair loss or promotion of hair growth.

In one embodiment of the invention, the concentration of the compound of Formula (I) or salt thereof in a total pharmaceutical composition or cosmetic composition may be 0.001 to 5 ppm.

If the concentration of the compound of Formula (I) is less than 0.001 ppm, the effect of prevention or treatment of hair loss or promotion of hair growth may not be enough. To the contrary, if the concentration is more than 5 ppm, cytotoxicity can be a problem. As a specific example, the concentration of the compound of Formula (I) is preferably 0.005 to 3 ppm. Further, in consideration of both safety and effect of prevention or treatment of hair loss or promotion of hair growth, the concentration of the compound of Formula (I) may be preferably 0.01 to 2 ppm.

The pharmaceutical composition or cosmetic composition according to the present invention can maintain calcium concentration in human hair dermal papilla cells stably for 60 min or more by comprising the compound of Formula (I) or salt thereof even if intracellular pH of human hair dermal papilla cells is neutral or basic of 7 to 9. As a specific example, the pharmaceutical composition or cosmetic composition according to the present invention can maintain calcium concentration stably for 60 to 120 min and thus has an advantage of long-lasting effect compared to conventional compositions.

In one embodiment of the invention, the compound of Formula (I) or salt thereof can promote differentiation and proliferation of hair follicle stem cells and hair dermal papilla cells by stably maintaining calcium concentration in human hair dermal papilla cells and activating Wnt/β-catenin signal transduction pathway.

Further, the pharmaceutical composition or cosmetic composition according to the present invention can enhance the effect of prevention or treatment of hair loss or promotion of hair growth by further comprising stem cell components (one or more selected from the group consisting of a growth factor, noggin, an amino acid, a long chain fatty acid, an active factor and a water-soluble vitamin) in addition to the compound of Formula (I) or salt thereof.

The compound having the structure of Formula (I) may be provided as a free substance, as well as a pharmaceutically acceptable salt, solvate, polymorph, and prodrug thereof. Moreover, the compound having the structure of Formula (I) or salt thereof is not particularly limited as long as it is in a form that can be compounded in a medicine or cosmetics.

In one embodiment of the present invention, the amino acid may be selected from the group comprising alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine, and the salt of the amino acid is not limited as long as it is a pharmaceutically acceptable salt.

As used herein, the term "growth factor" refers to a polypeptide having a function of promoting division, growth and differentiation of various cells in a human body, and includes those obtained by synthesis through gene recombination or extraction.

In one embodiment of the present invention, the growth factor may be one or more selected from the group comprising an epithelial growth factor (EGF), an acidic fibroblast growth factor (FGF (a)), a basic fibroblast growth factor (FGF (b)), a vascular endothelial growth factor (VEGF), a platelet-derived growth factor (PDGF) and a keratinocyte growth factor (KGF). The present composition can improve effect of maintaining a normal growth cycle through activating Wnt/β-catenin signal transduction pathway by comprising these growth factors.

As used herein, the term "noggin" refers to a protein that is involved in the development of nerve tissues, muscles, and bones among human tissues, and noggin may be obtained through a method known in the art.

In one embodiment of the present invention, although the long-chain fatty acid is not particularly limited as long as it is a saturated or unsaturated C8 to C18 long chain fatty acid, the long-chain fatty acid may be selected from the group comprising linolenic acid, myristic acid, oleic acid and palmitic acid. And the salt of the long-chain fatty acid is not particularly limited as long as it is pharmaceutically acceptable.

In one embodiment of the present invention, the active factor may be one or more selected from the group comprising inositol, adenine, glutathione and cholesterol.

In one embodiment of the present invention, the water-soluble vitamins may be one or more selected from the group comprising thiamine (B1), riboflavin (B2), niacinamide (B3), pantothenic acid (B5), pyridoxine (B6), biotin (B7), folic acid (B9), cyanocobalamin (B12) and ascorbic acid (C), and the salt of the water-soluble vitamin is not particularly limited as long as it is pharmaceutically acceptable.

In one embodiment of the present invention, the pharmaceutical or cosmetic composition may comprise the compound having the structure of Formula (I) above or salt thereof, one or more nature-derived amino acid or salt thereof, a mixture comprising one or more growth factor and noggin, one or more saturated or unsaturated C8 to C18 long chain fatty acid or salt thereof, one or more active factor, and one or more water-soluble vitamin or salt thereof.

In one embodiment of the present invention, the pharmaceutical composition or cosmetic composition may comprise the compound having the structure of Formula (I) or salt thereof in an amount of $10^{-7}$ to $5\times10^{-4}$% by weight, preferably $10^{-6}$ to $2\times10^{-4}$% by weight, based on the total weight of the composition.

In one embodiment of the present invention, the pharmaceutical composition or cosmetic composition may comprise the amino acid or salt thereof in an amount of $10^{-3}$ to $5\times10^{-1}$% by weight, preferably $10^{-2}$ to $1.5\times10^{-1}$% by weight, more preferably $4\times10^{-2}$ to $1.2\times10^{-1}$% by weight, based on the total weight of the composition, and this amount may be properly adjusted depending on the conditions of production and formulation.

In one embodiment of the present invention, the pharmaceutical composition or cosmetic composition may comprise a mixture comprising the growth factor and noggin in an amount of $10^{-5}$ to $5\times10^{-2}$% by weight, preferably $10^{-4}$ to $10^{-2}$% by weight, based on the total weight of the composition.

In one embodiment of the present invention, the pharmaceutical composition or cosmetic composition may comprise the long chain fatty acid or salt thereof in an amount of $10^{-4}$ to $5\times10^{-2}$% by weight, preferably $5\times10^{-4}$ to $10^{-2}$% by weight, based on the total weight of the composition.

In one embodiment of the present invention, the pharmaceutical composition or cosmetic composition may comprise the active factor in an amount of $10^{-4}$ to $5\times10^{-2}$% by weight, preferably $5\times10^{-4}$ to $10^{-2}$% by weight, based on the total weight of the composition.

In one embodiment of the present invention, the pharmaceutical composition or cosmetic composition may comprise the water-soluble vitamin or salt thereof in an amount of $10^{-4}$ to $5\times10^{-2}$% by weight, preferably $5\times10^4$ to $10^{-2}$% by weight, based on the total weight of the composition.

In one embodiment of the present invention, the pharmaceutical composition or cosmetic composition may comprise the amino acid in an amount of 4000 parts by weight to 40000 parts by weight, preferably 16000 parts by weight to 40000 parts by weight, based on 100 parts by weight of the growth factor and noggin, the water-soluble vitamin or salt thereof in an amount of 240 parts by weight to 4000 parts by weight, preferably 1000 parts by weight to 4000 parts by weight, based on 100 parts by weight of the growth factor and noggin, the active factor in an amount of 80 parts by weight to 1600 parts by weight, preferably 160 parts by weight to 800 parts by weight, based on 100 parts by weight of the growth factor and noggin, the long chain fatty acid or salt thereof in an amount of 200 parts by weight to 3200 parts by weight, preferably 400 parts by weight to 1600 parts by weight, based on 100 parts by weight of the growth factor and noggin, and the growth factor in an amount of 6.25 parts by weight to 125 parts by weight, preferably 12.5 parts by weight to 50 parts by weight, based on 100 parts by weight of the active factor.

In one embodiment of the present invention, the growth factor comprises an epithelial growth factor (EGF), an acidic fibroblast growth factor (FGF (a)), a basic fibroblast growth factor (FGF (b)), a vascular endothelial growth factor (VEGF), a platelet-derived growth factor (PDGF) and a keratinocyte growth factor (KGF). Further, the weight ratio of epithelial growth factor (EGF):acidic fibroblast growth factor (FGF (a)):basic fibroblast growth factor (FGF (b)):vascular endothelial growth factor (VEGF):platelet-derived growth factor (PDGF):keratinocyte growth factor (KGF):noggin in the pharmaceutical or cosmetic composition may be 0.1 to 10:0.1 to 10:0.1 to 10:0.1 to 10:0.1 to 10:0.1 to 10:0.1 to 10, preferably 2 to 6:4 to 8:4 to 8:1 to 2:1 to 2:1 to 2:1 to 2, and more preferably 2 to 4:2 to 6:2 to 6:2 to 6:2 to 6:2 to 6:2 to 6.

In one embodiment of the present invention, the weight ratio of amino acid or salt thereof:long chain fatty acid or salt thereof:active factor:water-soluble vitamin or salt thereof in the pharmaceutical composition or cosmetic composition may be 100 to 2000:10 to 200:5 to 200:10 to 200.

In one embodiment of the present invention, the pharmaceutical or cosmetic composition may further comprise suitable carriers, excipients and diluents conventionally used in the manufacture of pharmaceutical compositions or cosmetic compositions.

In particular, the composition is formulated using diluents or excipients such as pharmaceutically acceptable fillers, extenders, binders, humectants, disintegrants, surfactants and the like which are generally used. In addition, anticoagulants, lubricants, fragrances, emulsifiers, preservatives, and the like may be added, and the composition may be formulated using methods well known in the art to provide rapid, sustained, or delayed release of the active ingredient after administration to a mammal.

The pharmaceutical or cosmetic composition according to the present invention may be formulated into a conventional pharmaceutical formulation known in the art, and preferably it may be formulated into a transdermal preparation and an external preparation for skin by topical application.

In one embodiment of the present invention, the pharmaceutical or cosmetic composition according to the present invention may be an external preparation for skin, and can be formulated into any possible formulations applicable to skin, especially, scalp, such as ointment, paste, gel, jelly, serum, aerosol spray, non-aerosol spray, foam, cream, lotion, solution or suspension.

The pharmaceutical or cosmetic composition according to the present invention can be administered once or twice a day by topical application to a site where prevention or treatment of hair loss, or promotion of hair growth is desired. The daily application amount of the composition is about 0.5 to 3 mg/cm$^2$ (skin surface area) based on 1 wt % of the active ingredient, and may be increased or decreased depending on the area of the application site. The dose and the frequency of administration can be appropriately increased or decreased according to the patient's age, sex, and degree of progress of hair loss.

On the other hand, the cosmetic composition according to the present invention may be applied in any possible formulations applied to the skin, particularly scalp. More specifically, the composition may be prepared in a formulation such as a hair tonic, a hair conditioner, a hair essence, a hair lotion, a hair nutrition lotion, a hair shampoo, a hair rinse, a hair treatment, a hair cream, a hair nutrition cream, a hair moisturizing cream, a hair massage cream, a hair wax, a hair aerosol, a hair pack, a hair nutrition pack, a hair soap, a hair cleansing foam, a hair oil, a hair drying agent, an agent for preserving hair, a hair dye, a hair waving agent, a hair bleaching agent, a hair gel, a hair glaze, a hair dressinger, a hair lacquer, a hair moisturizer, a hair mousse or a hair spray. In addition, it can also be prepared as a skin-contacting substance that comes into contact with a skin, such as cosmetics, detergents, and fibers.

In one embodiment of the present invention, additives can be appropriately selected and blended with the cosmetic composition by those skilled in the art within a range not to impair the purposes and effects of the present invention. Examples of the additives that can be blended include an oil and fat component, a moisturizer, an emollient, a surfactant, organic and inorganic pigments, an organic powder, an ultraviolet absorber, a preservative, a bactericide, an antioxidant, a plant extract, a pH adjuster, an alcohol, a dye, fragrances, a blood circulation promoter, a skin cooling agent, an anhydrotics, purified water and the like.

MODE FOR THE INVENTION

Hereinafter, the present invention will be described in more detail by way of examples. It will be apparent to those skilled in the art that the following examples are illustrative only and various changes and modifications may be made without departing from the spirit and scope of the invention, and such changes and modifications are also within the scope of the appended claims.

Preparation Example 1. Preparation of a cADPR Mixture and cADPR Mixture Solutions Cyclic ADP Ribose (cADPR)(C202 SIGMA, CAS Number: 119340-53-3) purchased from Sigma-Aldrich (USA) was mixed with a medium in which a phospholipid, a lecithin, an oleic acid, and a caprylyl glycol are mixed in a weight ratio of 1:1:0.05:0.05, and then the mixture was homogenated with a high-speed homogenizer to provide a cADPR mixture of Preparation Example 1.

Further, the obtained cADPR mixture was added to 1 L of purified water to provide cADPR mixture solutions of Preparation Examples 1-1 to 1-8 having cADPR contents as described in Table 1 below.

TABLE 1

| | Preparation Example 1-1 | Preparation Example 1-2 | Preparation Example 1-3 | Preparation Example 1-4 | Preparation Example 1-5 | Preparation Example 1-6 | Preparation Example 1-7 | Preparation Example 1-8 |
|---|---|---|---|---|---|---|---|---|
| Amount of cARDP(ppm) | 0.01 | 0.05 | 0.1 | 0.5 | 1.0 | 2.0 | 0.005 | 0.001 |

Comparative Preparation Example 1. Preparation of a NAADP Liposome Mixture and NAADP Liposome Mixture Solutions NAADP was prepared according to the method described in "Acidic residues at the active sites of CD38 and ADP-ribosyl cyclase determine nicotinic acid adenine dinucleotide phosphate (NAADP) synthesis and hydrolysis activities". The Journal of Biological Chemistry. 281 (39): 28951-7, using NADP (nicotinamide adenine dinucleotide phosphate), nicotinic acid (NA) and ADP-ribosyl cyclase purchased from Sigma-Aldrich (USA). The prepared NAADP was mixed with a medium prepared by mixing a phospholipid, lecithin, oleic acid, and caprylyl glycol in a ratio of 1:1:0.05:0.05, and then the mixture was homogenized with a high-speed homogenizer to provide a NAADP liposome mixture of Comparative Preparation Example 1.

Further, the obtained NAADP liposome mixture was added to 1 L of purified water to provide NAADP liposome mixture solutions of Comparative Preparation Examples 1-1 and 1-2 having NAADP contents as described in Table 2 below.

TABLE 2

| | Comparative Preparation Examples 1-1 | Comparative Preparation Examples 1-2 |
|---|---|---|
| Amount of NAADP(ppm) | 0.1 | 0.5 |

Examples

Pharmaceutical compositions according to the present invention were prepared by a known method in accordance with the compositions described in Table 3 to Table 5. Specifically, a mixture of growth factors (an epithelial growth factor (EGF), an acidic fibroblast growth factor (FGF (a)), a basic fibroblast growth factor (FGF (b)), a vascular endothelial growth factor (VEGF), a platelet-derived growth factor (PDGF) and a keratinocyte growth factor (KGF)) and noggin and a mixture of an amino acid, a long chain fatty acid, an active factor and a water-soluble vitamin were added to 1 L of purified water, and the resulting mixture was mixed with the above obtained cADPR or NAADP mixture to provide pharmaceutical compositions of Examples 1 to 11 and Comparative Examples 1 to 3.

At this time, the composition of Comparative Example 1 was prepared in the same manner as in Example 1 except for not comprising a cADPR mixture. The compositions of Comparative Examples 2 and 3 were prepared in the same manner as in Example 1 except for comprising a NAADP mixture instead of the cADPR mixture.

Further, the growth factors and noggin were prepared in accordance with the criteria for the use in cosmetics or pharmaceuticals of the Korean Ministry of Food and Drug Safety and INCI [International nomenclature cosmetic ingredient] of US PCPC (Personal care products councils). The growth factors and noggin were synthesized by recombining human-derived genes into E. coli. Their contents were measured by SDS-PAGE and HPLC and they were mixed using a high-speed homogenizer.

Meanwhile, the amino acids, the long chain fatty acids, the active factors and the water-soluble vitamins were prepared in accordance with the criteria for the use in cosmetics or pharmaceuticals of Korean Ministry of Food and Drug Safety. The amino acids in Table 3 to Table 5 are compositions in which alanine, arginine HCl, asparagine, aspartic acid, cysteine HCl, glutamic acid, glutamine, glycine, histidine HCl, isoleucine, leucine, lysine HCl, methionine, phenylalanine, proline, serine, threonine, tryptophan, tyrosine, and valine are evenly blended on a weight basis. Vitamins, active factors and fatty acids were also blended evenly on the basis of weight. Standard error of content for each component was less than 10%.

TABLE 3

| components (unit: ppm) | Example 1 | Example 2 | Example 3 | Example 4 | Example 5 |
|---|---|---|---|---|---|
| cADPR | 0.01 | 0.01 | 0.01 | 0.01 | 0.01 |
| NAADP | — | — | — | — | — |
| EGF | 1 | 0.5 | 1 | 0.5 | 1 |
| FGF(a) | 1.5 | 1 | 0.5 | 1 | 0.5 |
| FGF(b) | 1.5 | 1 | 0.5 | 1 | 0.5 |
| VEGF | 0.25 | 0.5 | 0.25 | 0.5 | 0.25 |
| PDGF | 0.25 | 0.5 | 0.25 | 0.5 | 0.25 |
| KGF | 0.25 | 0.5 | 1 | 0.25 | 0.5 |
| noggin | 0.25 | 0.5 | 1 | 0.25 | 0.5 |
| amino acid | 400 | 400 | 400 | 400 | 400 |
| biotin(B7) | 20 | 20 | 20 | 20 | 20 |
| vitamin | 5 | 5 | 5 | 5 | 5 |
| active factor | 10 | 10 | 10 | 10 | 10 |
| long chain fatty acid | 20 | 20 | 20 | 20 | 20 |

TABLE 4

| components (unit: ppm) | Example 6 | Example 7 | Example 8 | Example 9 | Example 10 | Example 11 |
|---|---|---|---|---|---|---|
| cADPR | 0.01 | 0.5 | 1.0 | 0.01 | 0.01 | 0.01 |
| NAADP | — | — | — | — | — | — |
| EGF | 1 | 1 | 1 | 1 | 1 | 1 |
| FGF(a) | 1.5 | 1.5 | 1.5 | 1.5 | 1.5 | 1.5 |
| FGF(b) | 1.5 | 1.5 | 1.5 | 1.5 | 1.5 | 1.5 |
| VEGF | 0.25 | 0.25 | 0.25 | 0.25 | 0.25 | 0.25 |
| PDGF | 0.25 | 0.25 | 0.25 | 0.25 | 0.25 | 0.25 |

TABLE 4-continued

| components (unit: ppm) | Example 6 | Example 7 | Example 8 | Example 9 | Example 10 | Example 11 |
|---|---|---|---|---|---|---|
| KGF | 0.25 | 0.25 | 0.25 | 0.25 | 0.25 | 0.25 |
| noggin | 0.25 | 0.25 | 0.25 | 0.25 | 0.25 | 0.25 |
| amino acid | 600 | 600 | 600 | 800 | 1000 | 1200 |
| biotin(B7) | 30 | 30 | 30 | 40 | 50 | 60 |
| vitamin | 6 | 6 | 6 | 7 | 8 | 9 |
| active factor | 20 | 20 | 20 | 40 | 60 | 100 |
| long chain fatty acid | 40 | 40 | 40 | 60 | 80 | 100 |

TABLE 5

| components (unit: ppm) | Comparative Example 1 | Comparative Example 2 | Comparative Example 3 |
|---|---|---|---|
| cADPR | — | — | — |
| NAADP | — | 0.1 | 0.5 |
| EGF | 1 | 1 | 1 |
| FGF(a) | 1.5 | 1.5 | 1.5 |
| FGF(b) | 1.5 | 1.5 | 1.5 |
| VEGF | 0.25 | 0.25 | 0.25 |
| PDGF | 0.25 | 0.25 | 0.25 |
| KGF | 0.25 | 0.25 | 0.25 |
| noggin | 0.25 | 0.25 | 0.25 |
| amino acid | 400 | 400 | 400 |
| biotin(B7) | 20 | 20 | 20 |
| vitamin | 5 | 5 | 5 |
| active factor | 10 | 10 | 10 |
| long chain fatty acid | 20 | 20 | 20 |

Formulation Examples—Preparation of Cosmetic Compositions

Cosmetic compositions of Formulation Example 1 and 2 and Comparative Formulation Examples 1 and 2 having compositions in accordance with Table 6 below were prepared by using the cADPR mixture of Preparation Example 1 and the pharmaceutical compositions of Example 1 and Example 7. The following Formulation Examples are intended to describe the present invention more specifically, but not to limit the scope of the invention.

TABLE 6

| (weight %) | Comparative Formulation Example 1 | Comparative Formulation Example 2 | Formulation Example 1 | Formulation Example 2 |
|---|---|---|---|---|
| purified water | 52.9 | 52.89 | 41.9 | 40.9 |
| glycerin | 3 | 3 | 3 | 3 |
| EDTA-Na | 0.05 | 0.05 | 0.05 | 0.05 |
| Amisoft CS-22 | 30 | 30 | 30 | 30 |
| Miconate LES | 12 | 12 | 12 | 12 |
| citric acid | 0.1 | 0.1 | 0.1 | 0.1 |
| phenoxy ethanol | 0.7 | 0.7 | 0.7 | 0.7 |
| ethylhexylglycerin | 0.05 | 0.05 | 0.05 | 0.05 |
| cADPR mixture (Preparation Example 1-1) | — | 0.01 | 0.5 | 0.01 |
| pharmaceutical composition | — | — | 11(Example 7) | 11.95(Example 1) |
| NaCl | 1 | 1 | 1 | 1 |
| Perfume | 0.2 | 0.2 | 0.2 | 0.2 |
| total | 100 | 100 | 100 | 100 |

Experimental Example 1—Test for Cytotoxicity of cADPR in Human Hair Dermal Papilla Cells To confirm cytotoxicity of cADPR in human hair dermal papilla cells (HHDPC), MTT assay which is a representative method for measuring cytotoxicity and determines cytotoxicity by measuring mitochondrial reducing power by dehydrogenase action was conducted.

Human hair dermal papilla cells were cultured in an HDP kit medium (Human hair dermal papilla cell media kit) at 37° C. in a 5% $CO_2$ incubator (manufactured by Thermo Fisher Scientific, USA).

The cultured cells were dispensed into a 24-well plate at a concentration of $3 \times 10^4$ cells/well. After 18 hours, the cADPR mixture solutions according to Preparation Examples 1-1 to 1-6 (0.01, 0.05, 0.1, 0.5, 1 and 2 ppm, respectively) were added to each well. Then, the cells were cultured in the 5% $CO_2$ incubator at 37° C. for 48 hours. After 48 hours of the incubation, each well was washed once with PBS (phosphate buffered saline) solution, and added with 50 μl of 5 mg/mL MTT reagent (Sigma, USA) and 450 μl of fresh medium. The wells were incubated for 2.5 hours and then supernatants were removed. When formazan crystals were observed in each well, DMSO (dimethylsulfoxide) was added and shaken for 30 minutes in the dark to dissolve the formazan crystal, and then the absorbance was measured at 750 nm using a spectrophotometer.

Since the measured absorbance shows the amount of MTT reduced by the cells and the amount is proportional to the number of survival human hair dermal papilla cells in each well, cell viability indicating cytotoxicity was calculated from the absorbance. The results of the calculation are shown in Table 7 and FIG. 1, and it was confirmed that no cytotoxicity was observed when cADPR was treated in the concentration range according to the present invention.

TABLE 7

|  | Preparation Example 1-1 | Preparation Example 1-2 | Preparation Example 1-3 | Preparation Example 1-5 | Preparation Example 1-6 |
|---|---|---|---|---|---|
| cell viability(%) | 100 | 100 | 100 | 98 | 98 |

Experimental Example 2. Evaluation of Effect of β-Catenin Expression Induction by Using cADPR Mixture Solution in Human Hair Dermal Papilla Cells The effect of cADPR to induce expression of β-catenin in human hair dermal papilla cells was confirmed by examination of transcription activity of T cell factor (TCF) using TOPFlash luciferase reporter assay (Promega).

Human hair dermal papilla cells were cultured in the same manner as in Experimental Example 1.

The cultured human hair dermal papilla cells were dispensed in a 6-well plate at a concentration of $1 \times 10^5$ cells/well. After 18 hrs, the cells were transformed by using transformation vector such as 0.3 μg/ml of pTOPFLASH harboring neomycin resistance gene and 1 μg/ml of pFOP-FLASH and treated with neomycine-based antibiotic G418 to select transformed cells.

The transformed cells were treated with each cADPR mixture solution of Preparation Example 1-1 to Preparation Example 1-4 and cultured in a serum-free medium for 24 hrs. And then, the cultured cells were washed with PBS twice and lysed with Reporter lysis buffer (Promega). Then, luciferase activity was measured using Luciferase activity assay kit (Promega).

The measured results are shown in FIG. 2 indicating that the cADPR mixture solutions of the present invention have an effect of inducing expression of β-catenin and an activity of TOPFLASH luciferase reporter changes with the concentration of β-catenin.

Experimental Example 3. Measurement of Expression Levels of Genes Related to Prevention of Hair Loss or Promotion of Hair Growth by Using cADPR Mixture Solution in Human Hair Dermal Papilla Cells Expression levels of genes related to prevention of hair loss or promotion of hair growth, such as lymphoid enhancer-binding factor 1 (LEF-1, ThermoFisher Scientific, Hs01547250_m1), and transforming growth factor (TGF-β2, ThermoFisher Scientific, Hs00234244_m1), caused by cADPR in human hair dermal papilla cells were measured.

LEF-1 is a gene related to prevention of hair loss or promotion of hair growth and TGF-β2 is a gene inducing categen phase and suppressing growth of hair follicle.

Human hair dermal papilla cells was cultured in the same manner as in Experimental Example 1, and the cultured human hair dermal papilla cells were dispensed in a 6-well plate at a concentration of $3 \times 10^5$ cells/well. 18 hrs later, cADPR mixture solutions of Preparation Examples 1-1 to 1-3, 1-7 and 1-8 were treated respectively along with 10 nM of dihydrotestosterone (DHT). After 24 hrs, RNA was isolated from the cells and cDNA was synthesized using PCR (Applied Biosystems, USA). Changes of the levels of the related genes were measured by realtime PCR using TaqMan assay (Life Technologies) with a synthesized cDNA TaqMan™ probe and expression levels of LEF-1 and TGF-β2 could be measured from the levels of the genes.

The measured results are shown in FIGS. 3 and 4, and it can be seen from the results that when the cADPR mixture solutions according to the present invention are used, the expression of LEF-1 gene is increased and the expression of TGF-β2 gene is suppressed. Further, it is confirmed that the expression levels of these genes change with the concentration of cADPR in the mixture.

Experimental Example 4. Measurement of Expression Levels of Genes Related to Prevention of Hair Loss or Promotion of Hair Growth Caused by a Pharmaceutical Composition Comprising cADPR in Human Hair Dermal Papilla Cells Expression levels of genes related to prevention of hair loss or promotion of hair growth were measured in the same manner as in Experimental Example 3, except that the pharmaceutical compositions of Examples 1 to 8 and Comparative Examples 1 to 3 were used instead of the cADPR mixture solutions of Preparation Examples 1-1 to 1-3, 1-7 and 1-8. The results are shown in Tables 8 and 9. The values in Tables 8 and 9 represent the relative expression level based on a standard of 1 of the gene expression level of untreated human hair dermal papilla cells.

TABLE 8

| | Relative quantification of TGF-β2/actin mRNA |
|---|---|
| Example 1 | 0.5 |
| Example 2 | 0.8 |
| Example 3 | 0.7 |
| Example 4 | 0.7 |
| Example 5 | 0.8 |
| Example 6 | 0.5 |
| Example 7 | 0.4 |
| Example 8 | 0.4 |
| Comparative Example 1 | 1.1 |
| Comparative Example 2 | 0.7 |
| Comparative Example 3 | 0.6 |

TABLE 9

| | Relative quantification of LEF-1/actin mRNA |
|---|---|
| Example 1 | 2.1 |
| Example 2 | 1.9 |
| Example 3 | 2.2 |
| Example 4 | 1.6 |
| Example 5 | 1.8 |
| Example 6 | 4.2 |
| Example 7 | 3.3 |
| Example 8 | 2.8 |
| Comparative Example 1 | 1.3 |
| Comparative Example 2 | 2.1 |
| Comparative Example 3 | 2.6 |

It can be confirmed from the Tables 8 and 9 that the compositions of Comparative Examples 2 and 3 comprising NAADP mixture as well as the pharmaceutical compositions of Examples 1 to 8 comprising cADPR mixture showed increased expression level of LEF-1 gene and suppressed expression level of TGF-β2 gene, whereas the composition of Comparative Example 1 not comprising cADPR or NAADP showed suppressed expression level of LEF-1 gene and increased expression level of TGF-β2 gene.

When the cADPR mixture was used, the changes in expression levels of LEF-1 and TGF-β2 genes were similar to the changes observed when NAADP mixture was used. However, as can be seen in Experimental Example 5 below, the cADPR mixture and the NAADP mixture differ in the duration time of calcium concentration in human hair dermal papilla cells. Thus, as shown in Experimental Example 6, a pharmaceutical composition comprising cADPR mixture exhibits more excellent effect for enhancing hair density.

Experimental Example 5. Test for Measuring the Duration Time of Calcium Concentration in Human Hair Dermal Papilla Cells by cADPR Mixture Solutions Changes in the duration time of calcium concentration in human hair dermal papilla cells depending on the concentration of cADPR and time were measured.

Human hair dermal papilla cells were cultured in the same manner as in Experimental Example 1. The cultured human hair dermal papilla cells were treated with cADPR mixture solutions of Preparation Examples 1-3 and 1-4 and NAADP liposome mixture solutions of Comparative Preparation Examples 1-1 and 1-2, respectively. After 10 min, 60 min and 120 min, culture solutions were harvested and quantified using inductively coupled plasma method. In particular, quantification was conducted by the method in which a mixture of spray sample (Teledyne leeman labs, USA) is spilled to generate plasma state electronically and the amount of light emission is measured and converted in comparison with the light emission of the reference material.

The measured results are shown in Table 10 and FIG. 5. From this result, it is confirmed that the cADPR mixture solution shows higher concentration of calcium than the NAADP mixture solution and maintains calcium secretion even after 120 min.

TABLE 10

| | after 10 min | after 60 min | after 120 min |
|---|---|---|---|
| Preparation Example 1-3 (cADPR, 0.1 ppm) | 55 | 95 | 115 |
| Preparation Example 1-4 (cADPR, 0.5 ppm) | 78 | 110 | 125 |
| Comparative Preparation Example 1-1 (NAADP, 0.1 ppm) | 34 | 70 | 46 |
| Comparative Preparation Example 1-2 (NAADP, 0.5 ppm) | 40 | 80 | 40 |

Experimental Example 6. Test of Hair Density in a Human Body

A test for the application of the pharmaceutical composition and the cosmetic composition of the present invention on a human body was conducted according to a guideline provided by Korea Ministry of Food & Drug Safety. The test was conducted for 24 weeks, and men and women diagnosed with androgenetic alopecia aged 18 to 54 years were selected as test subjects. Twenty subjects were respectively assigned to a test group and a control group.

For the test group, the pharmaceutical compositions of Examples 1 to 11 and the cosmetic compositions of Formulation Examples 1 and 2 were applied for 24 weeks. For the control group, the pharmaceutical compositions of Comparative Examples 1 to 3 and the cosmetic compositions of Comparative Formulation Examples 1 and 2 were applied for 24 weeks. And then hair densities were measured. The hair density was evaluated as a score of 1-10, and the results are shown in Table 11 below and FIG. 6.

For the hair density scores of Table 11 below, male test subjects showing 135 hairs/cm$^2$ or more and female test subjects showing 130 hairs/cm$^2$ or more were given hair density score of 10. Based on this criteria, the hair density score was given by subtracting 1 point each time as the hair density decreased by 10%.

TABLE 11

| | at 6 weeks | at 12 weeks | at 24 weeks |
|---|---|---|---|
| Example 1 | 7 | 8 | 9 |
| Example 2 | 5 | 7 | 9 |
| Example 3 | 6 | 7 | 9 |
| Example 4 | 5 | 6 | 9 |
| Example 5 | 6 | 8 | 10 |
| Example 6 | 7 | 9 | 10 |
| Example 7 | 7 | 8 | 10 |
| Example 8 | 6 | 9 | 10 |
| Example 9 | 6 | 7 | 9 |
| Example 10 | 5 | 6 | 9 |
| Example 11 | 5 | 6 | 9 |

TABLE 11-continued

|  | at 6 weeks | at 12 weeks | at 24 weeks |
|---|---|---|---|
| Comparative Example 1 | 2 | 2 | 3 |
| Comparative Example 2 | 3 | 4 | 5 |
| Comparative Example 3 | 4 | 5 | 6 |
| Formulation Example 1 | 6 | 8 | 10 |
| Formulation Example 2 | 7 | 8 | 9 |
| Comparative Formulation Example 1 | 2 | 2 | 3 |
| Comparative Formulation Example 2 | 5 | 6 | 7 | unit: score

Referring to Table 11 and FIG. 6, in the case of the pharmaceutical composition, the pharmaceutical composition of Comparative Example 1 had a density score of 3 or less even at 24 weeks. The pharmaceutical compositions of Comparative Example 2 and 3 showed scores of 4~6 which are higher than the scores of the pharmaceutical composition of Comparative Example 1 but are lower than the scores of the compositions of Examples 1 to 11. The compositions of Examples 1 to 11 showed high average hair density scores of 9 or more. Further, in the case of the cosmetic composition, the composition of Comparative Formulation Example 1 had a density score of 3 or less even at 24 weeks. The composition of Comparative Formulation Example 2 showed average density scores of 5~7 which are higher than the density scores of the composition of Comparative Formulation Example 1 but are lower than the scores of the composition of Formulation Examples 1 and 2. The compositions of Formulation Examples 1 and 2 showed average scores of 8 or more.

From this result, it is confirmed that the pharmaceutical composition and the cosmetic composition according to the present invention have more excellent effect for improving hair density by comprising cADPR mixture compared to the composition not comprising cADPR mixture or comprising NAADP mixture.

The invention claimed is:

1. A pharmaceutical composition for treating hair loss, or promoting hair growth, comprising a compound having a structure represented by the following Formula (I) or salt thereof:

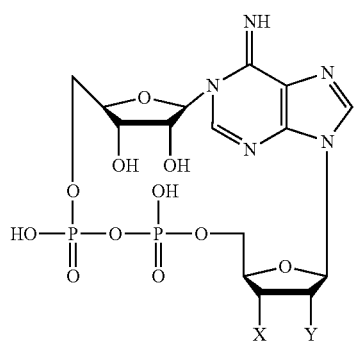

wherein,
X and Y are OH,
wherein the compound of Formula (I) is cyclic adenosine diphosphate ribose (cADPR),
wherein the concentration of the compound of Formula (I) or salt thereof in the composition is 0.001 to 5 ppm.

2. The pharmaceutical composition according to claim 1, further comprising at least one selected from the group consisting of one or more naturally occurring amino acid or salt thereof, one or more growth factor, noggin, one or more saturated or unsaturated C8 to C18 long chain fatty acid or salt thereof, one or more active factor and one or more water-soluble vitamin or salt thereof.

3. The pharmaceutical composition according to claim 1, wherein the compound of Formula (I) or salt thereof promotes differentiation and proliferation of hair follicle stem cells and hair dermal papilla cells by stably maintaining calcium concentration in the hair dermal papilla cells and activating Wnt/β-catenin signal transduction pathway.

4. The pharmaceutical composition according to claim 3, wherein the compound of Formula (I) or salt thereof maintains calcium concentration in the hair dermal papilla cells for 60 min to 120 min at pH of 7 to 9.

5. The pharmaceutical composition according to claim 2, comprising the compound having the structure of Formula (I) or salt thereof in an amount of $10^{-7}$ to $5\times10^{-6}$% by weight, the amino acid or salt thereof in an amount of $10^{-3}$ to $5\times10^{-1}$% by weight, the mixture comprising the growth factor and noggin in an amount of $10^{-5}$ to $5\times10^{-2}$% by weight, the long chain fatty acid or salt thereof in an amount of $10^{-4}$ to $5\times10^{-2}$% by weight, the active factor in an amount of $10^{-4}$ to $5\times10^{-2}$% by weight and the water-soluble vitamin or salt thereof in an amount of $10^{-4}$ to $5\times10^{-2}$% by weight based on the total weight of the composition.

6. The pharmaceutical composition according to claim 2, wherein the growth factor comprises an epithelial growth factor (EGF), an acidic fibroblast growth factor (FGF (a)), a basic fibroblast growth factor (FGF (b)), a vascular endothelial growth factor (VEGF), a platelet-derived growth factor (PDGF) and a keratinocyte growth factor (KGF), and the weight ratio of epithelial growth factor (EGF): acidic fibroblast growth factor (FGF (a)): basic fibroblast growth factor (FGF (b)): vascular endothelial growth factor (VEGF): platelet-derived growth factor (PDGF): keratinocyte growth factor (KGF): noggin in the composition is 0.1 to 10: 0.1 to 10: 0.1 to 10: 0.1 to 10: 0.1 to 10: 0.1 to 10: 0.1 to 10.

7. The pharmaceutical composition according to claim 2, wherein the weight ratio of amino acid or salt thereof: long chain fatty acid or salt thereof: active factor: water-soluble vitamin or salt thereof in the composition is 100 to 2000: 10 to 200: 5 to 200: 10 to 200.

8. The pharmaceutical composition according to claim 2, wherein the composition comprises
the amino acid in an amount of 4000 parts by weight to 40000 parts by weight based on 100 parts by weight of the growth factor and noggin,
the water-soluble vitamin or salt thereof in an amount of 240 parts by weight to 4000 parts by weight based on 100 parts by weight of the growth factor and noggin,
the active factor in an amount of 80 parts by weight to 1600 parts by weight based on 100 parts by weight of the growth factor and noggin,
the long chain fatty acid or salt thereof in an amount of 200 parts by weight to 3200 parts by weight based on 100 parts by weight of the growth factor and noggin, and the growth factor and noggin in an amount of 6.25 parts by weight to 125 parts by weight based on 100 parts by weight of the active factor.

9. The pharmaceutical composition according to claim 1, wherein the composition is in the form of an ointment, paste, gel, jelly, serum, aerosol spray, non-aerosol spray, foam, cream, lotion, solution or suspension.

* * * * *